United States Patent
Teringo

(10) Patent No.: US 7,063,683 B2
(45) Date of Patent: Jun. 20, 2006

(54) NON-MECHANICAL SYRINGE AND NEEDLE ASSEMBLY NEEDLE GUARD

(76) Inventor: William M. Teringo, 105 Loudon St., SW. Condo #3, Leesburg, VA (US) 20175

( * ) Notice: Subject to any disclaimer, the term of this patent is extended or adjusted under 35 U.S.C. 154(b) by 0 days.

(21) Appl. No.: 10/898,198

(22) Filed: Jul. 26, 2004

(65) Prior Publication Data

US 2006/0020245 A1 Jan. 26, 2006

(51) Int. Cl.
*A61M 5/00* (2006.01)
(52) U.S. Cl. ........................ 604/110; 604/263
(58) Field of Classification Search .............. 604/263
See application file for complete search history.

(56) References Cited

U.S. PATENT DOCUMENTS

| | | | |
|---|---|---|---|
| 4,248,246 A | 2/1981 | Ikeda | |
| 4,270,536 A | 6/1981 | Chen | |
| 4,468,223 A * | 8/1984 | Minagawa et al. | 604/199 |
| 4,710,170 A | 12/1987 | Haber et al. | |
| 4,735,311 A | 4/1988 | Lowe et al. | |
| 4,801,295 A | 1/1989 | Spenser | |
| 4,872,552 A | 10/1989 | Unger | |
| 4,973,315 A * | 11/1990 | Sincock | 604/192 |
| 4,986,817 A * | 1/1991 | Code | 604/192 |
| 5,026,345 A | 6/1991 | Teringo | |
| 5,084,027 A * | 1/1992 | Bernard | 604/192 |
| 5,322,165 A * | 6/1994 | Melker et al. | 206/366 |
| 5,484,413 A * | 1/1996 | Gevorgian | 604/110 |
| 5,505,705 A * | 4/1996 | Galpin et al. | 604/192 |

* cited by examiner

*Primary Examiner*—Nicholas D. Lucchesi
*Assistant Examiner*—Laura A. Bouchelle
(74) *Attorney, Agent, or Firm*—Siemens Patent Services, LC

(57) ABSTRACT

A non-mechanical needle guard for permanently securing and incapacitating a single used syringe and needle assembly consists of a sleeve for receiving the needle and luer lock and the hub end of a syringe. The sleeve contains a two part adhesive, the two elements being separated by a penetrable membrane, with the opened end of the sleeve being sealed by a second membrane. A stand holds a number of the needle guards in a stable, upright position so the needle may be inserted with a single hand, as required by OSHA. As the needle penetrates the two membranes, the two elements of the adhesive combine, permanently securing the needle and syringe end in the cured adhesive. The needle guard of the present invention secures and incapacitates the used needle and syringe in a manner meeting OSHA's disposal safety standards.

8 Claims, 6 Drawing Sheets

NON-MECHANICAL SYRINGE AND NEEDLE ASSEMBLY NEEDLE GUARD

BACKGROUND OF THE INVENTION

1. Field of the Invention

The present invention relates to a non-mechanical safety needle guard for preventing inadvertent needle punctures or sticks and for rendering a syringe and needle assembly useless after one use by capping the entire needle with the needle guard by use of a fast acting adhesive contained in the needle guard, and a supporting stand therefor. The combination of needle guard and stand constitute a single handed disposal system, as required by the Occupational Safety and Health Act (OSHA).

2. Description of the Prior Art

In light of widespread abuse of syringes and needles by drug addicts and the spread of AIDS associated with the use of or accidental puncture by contaminated needles, the prior inventions proposed syringe and needle assemblies with various safety features. To prevent reuse of discarded disposable syringe and needle assemblies and for preventing inadvertent needle punctures, many types of safety devices have been proposed.

U.S. Pat. No. 4,270,536, to Lemelson, discloses a needle breaking device. Specifically, after using the syringe and needle assembly, a plunger portion of the syringe is taken completely out of the syringe. The head of the plunger has a hole for holding the needle in place during breakage. However, this method or device is not safe, in that the fluid contained within the needle, which may be contaminated, becomes exposed to the person handling the syringe when the plunger is completely pulled out. Moreover, during the breaking process, the needle of the syringe may shatter, generating fragments which can stick the user and expose the user to potentially bio-hazardous material.

A second embodiment of the Lemelson patent discloses a sheath for encapsulating the needle by taking the plunger off the syringe and placing it over the needle. Again, because the plunger has to be taken off the syringe, contaminated fluid in the needle can expose the user. Furthermore, this device does not disable the syringe, as the plunger can be placed back into the syringe.

U.S. Pat. No. 4,248,246, to Ikeda discloses a cap for enclosing a needle portion of a sampling blood collector. The cap contains a seal material which is placed over the tip of the needle after it is used. However, Ikeda does not offer sufficient protection against subsequent accidents, because the cap can easily be pulled off.

U.S. Pat. No. 7,735,311, to Lowe, et al., is substantially similar to Ikeda, except that the Lowe patent relates to a syringe. A cap is used in the identical manner as the Ikeda patent to seal the needle and to prevent an inadvertent needle puncture.

U.S. Pat. No. 4,710,170, to Haber, et al., discloses a syringe assembly for preventing an accidental needle puncture and for rendering the syringe inoperable. Specifically, the entire needle assembly can be pulled into the syringe body. The plunger is then pushed directly into the needle portion until the needle completely embeds into the plunger. While this device completely disables the syringe and prevents an accidental needle puncture, once disabled, the shortcoming of this patent is that it cannot be used in conventional syringe and needle assemblies. On the other hand, the present invention is related to a protective sheath which can be used on any conventional assembly by simply capping the needle with the sheath, as opposed to the elaborate steps required by Haber. Also, the steps required in the Haber patent to disable the syringe may, in some instances be to complicated for ordinary individuals to follow.

U.S. Pat. No. 4,270,536, to Chen, discloses a syringe cap for disabling the syringe after one use. Specifically, a plug at the tip of the cap is slidable along the inner surface of the cap. By pushing in the plug, the needle will engage the tip portion of the needle to puncture the plug. The pulling the plunger causes adhesive contained within the plug to flow into the needle, thereby disabling the needle when the adhesive sets. The Chen patent has two drawbacks. First, the plug is easily pushed into the needle. Even a slight, inadvertent, push can cause the plug to engage the needle. The Chen patent provides no adequate measures for preventing the plug from being engaged accidentally. Second, the entire cap, along with the plug, can be pulled off, thereby exposing the needle for a possible needle injury. Further, the Chen patent does not provide any means for disabling the syringe portion.

U.S. Pat. No. 4,801,295, to Spenser, discloses a sleeve which slides along the outer body syringe surface. When the sleeve is fully extended, the needle is shielded, thereby avoiding an accidental needle puncture. While the sleeve is designed to be permanently locked in the extended safety position, the safety sleeve can be broken with force or can be severed from the syringe, thereby exposing the entire needle. Because the syringe and the needle are not disabled, the syringe and needle can be reused.

U.S. Pat. No. 4,872,552, to Unger, discloses a safety cap which is hinged to a syringe and needle assembly. When using the assembly, the cap is pivoted away from the needle portion. After using the assembly, the cap is placed back on the needle portion. The cap also includes a block slidably engaged therewith to enable the tip portion of the needle to penetrate the block, thus shielding the needle to prevent an accidental needle puncture. However, the shortcoming of the Unger invention is that the assembly is not disabled. Anyone can remove the cap from the assembly and reuse the assembly.

U.S. Pat. No. 5,026,345, to Teringo, discloses a non-mechanical locking incapacitation syringe safety needle guard for preventing reuse of a syringe and needle assembly and for preventing an accidental needle puncture. The needle guard has a hollow chamber filled with a liquid adhesive. When the needle portion, luer lock and neck of the syringe are placed in the chamber, the adhesive locks the needle guard permanently to the syringe, thereby disabling the needle portion. Furthermore, the adhesive is drawn into the syringe chamber to lock the plunger of the syringe to the syringe, thereby immobilizing the plunger, rendering the syringe and needle completely useless. The present invention utilizes a two part adhesive, which cures more quickly and solidly than the single part adhesive of Teringo, as well as providing relief grooves to allow the adhesive to flow more freely around the luer lock and hub of the syringe. Furthermore, with the improved bonding of the syringe to the needle guard by the two part adhesive of the present invention, in contrast to Teringo, the present invention does not need to fill the syringe with adhesive, as did the original.

Typically, used syringes and needles are first collected in mass quantities in a secure container, such as a Sharps container. Once collected, they are destroyed or disposed of by one of several methods. For instance, needle choppers, autoclaves and incineration have been used to destroy or dispose of used syringes and needles. However, these methods are not entirely satisfactory, in that the syringes and needle assemblies are not rendered useless immediately after their use. This provides an opportunity for individuals to pilfer syringes and needles during the collection process. By providing a needle guard in the present invention to permanently and immediately render the syringe and needle useless, even if the discarded and disabled syringes and needles are pilfered during collection, they cannot be reused.

With the exception of Teringo, the prior inventions do not provide a non-mechanical device for immediately rendering the syringe and needle completely inoperative by using adhesive in the needle guard. Rather, they require a safety device to be part of the original needle assembly package and are either of a mechanical locking nature or require force to break the needle portion of the syringe. None of the prior inventions encompasses the entire range of safety and permanence of the present invention which renders all functional parts of the syringe completely inoperative in a single handed process, as required by OSHA.

None of the above inventions and patents, taken either singly or in combination, is seen to describe the instant invention as claimed.

SUMMARY OF THE INVENTION

The present invention provides a non-mechanical needle guard which is quite similar to conventional shipping guards, with the exception that the guard of the present invention contains a fast curing, dual part adhesive for encapsulating the used needle and syringe hub. Additionally, a supporting stand holds the needle guard in a steady position, allowing single handed use of the guard, as required by OSHA. A penetrable membrane (typically foil) within the needle guard separates the activator element and the base element of the adhesive to prevent premature mixing and hardening of the adhesive within the needle guard. A second membrane seals the top of the guard.

After use, a needle is inserted into the needle guard, penetrating both the outer and inner membrane as it passes into the guard. Puncturing the inner membrane allows the activator and base elements of the adhesive to mix and harden almost instantaneously, permanently encapsulating the needle, luer lock and syringe hub within the needle guard. Utilization of the stand to hold the needle guard stationary allows the procedure to be completed with only one hand, as required by OSHA.

In a secondary embodiment, the disposal needle guard of the present invention may be formed as an integral part of the shipping needle guard. In this embodiment, the guard has two chambers, the shipping guard, which is placed over the needle at the time of manufacture and the adhesive filled disposal guard, into which the needle is inserted after use.

Accordingly, it is a principal object of the invention to provide a needle guard for a syringe and needle assembly to prevent an inadvertent needle puncture and for rendering the assembly completely inoperable immediately after use.

Yet another object of the invention is to provide a needle guard which renders a syringe and needle assembly inoperable virtually instantaneously.

It is another object of the invention to provide a needle guard, which does not require sterilization, for use with any conventional, disposable syringe and needle assembly.

Still another object of the invention is to provide a needle guard which, when used with an accompanying support stand allows single handed uses, as required by OSHA.

An additional object of the invention is to provide a needle guard and support stand which are easy and effective to use.

It is again an object of the invention to provide a needle guard and support stand which are economical to use.

Still another object of the invention is to provide a needle guard which eliminates the necessity to store functioning needle and syringe assemblies prior to disabling.

It is a further object of the invention to provide a needle guard, supplied with a syringe and needle assembly, where the needle guard serves two functions, one to serve as a conventional needle guard, and another to serve as a syringe and needle assembly immobilizer.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
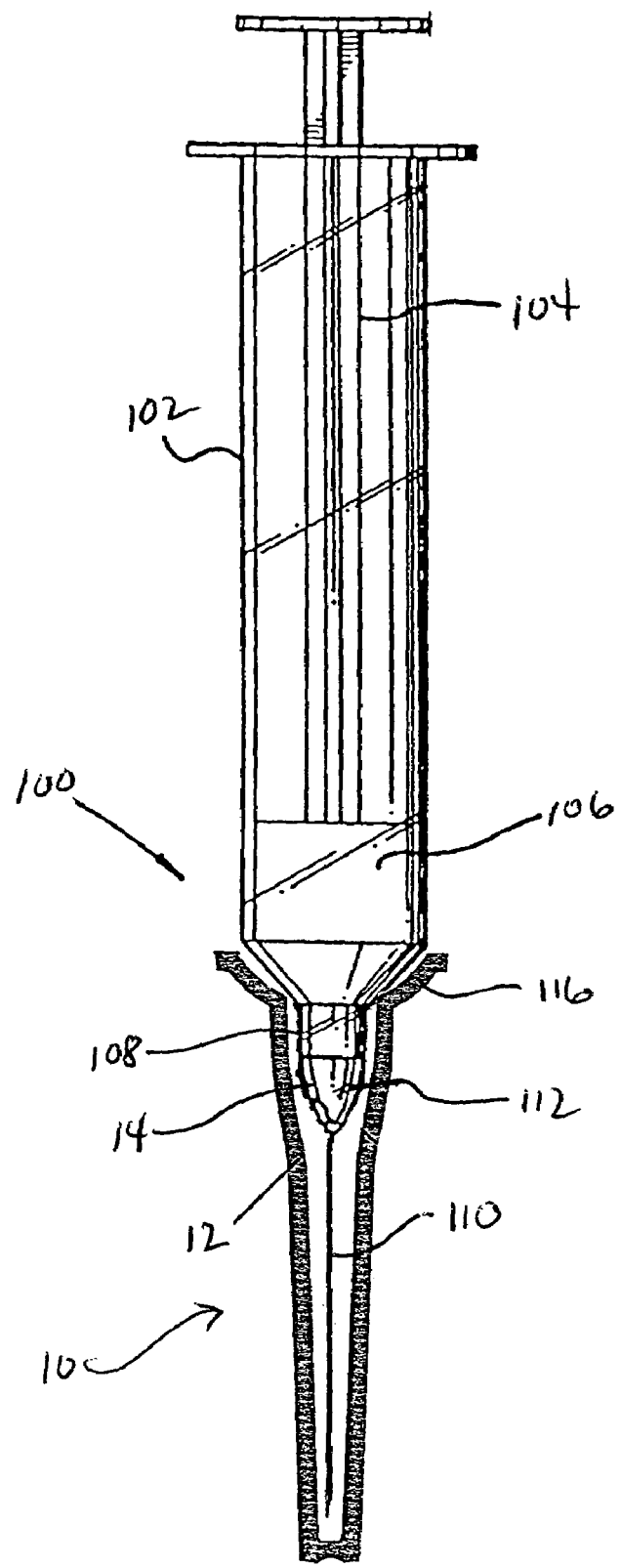
FIG. 1 is a cross sectional view of a syringe and needle assembly with the needle guard of a first embodiment of the present invention in place.

At FIG. 1, a typical syringe and needle assembly 100 is depicted as disposed of in a needle guard 10 of the present invention. The needle and syringe assembly 100 typically consists of a syringe body 102, a plunger 104 with a rubber plunger head 106, and a hub 108. The needle 110 has a luer lock 112 at its upper head which joins the needle 110 to the syringe hub 108. The connection between the hub 108 and luer lock 112 is typically a removable connection, although, in today's disposable needles, they are rarely separated, except possibly in the disposal process.

Figure 3:
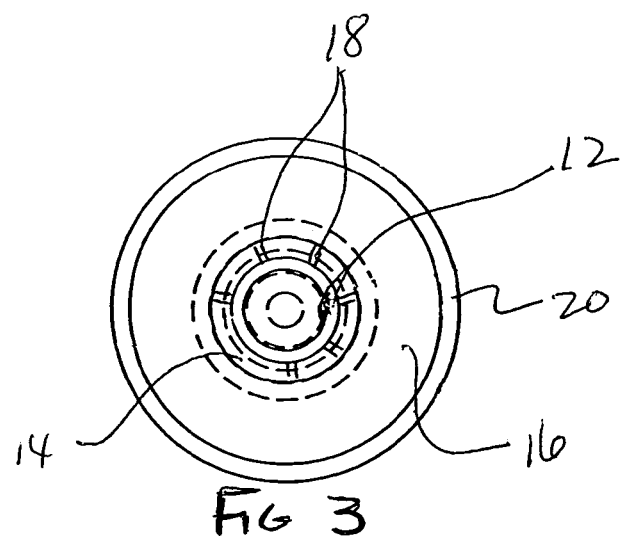
FIG. 3 is a top plan view of the needle guard of FIG. 1.
Figure 2:
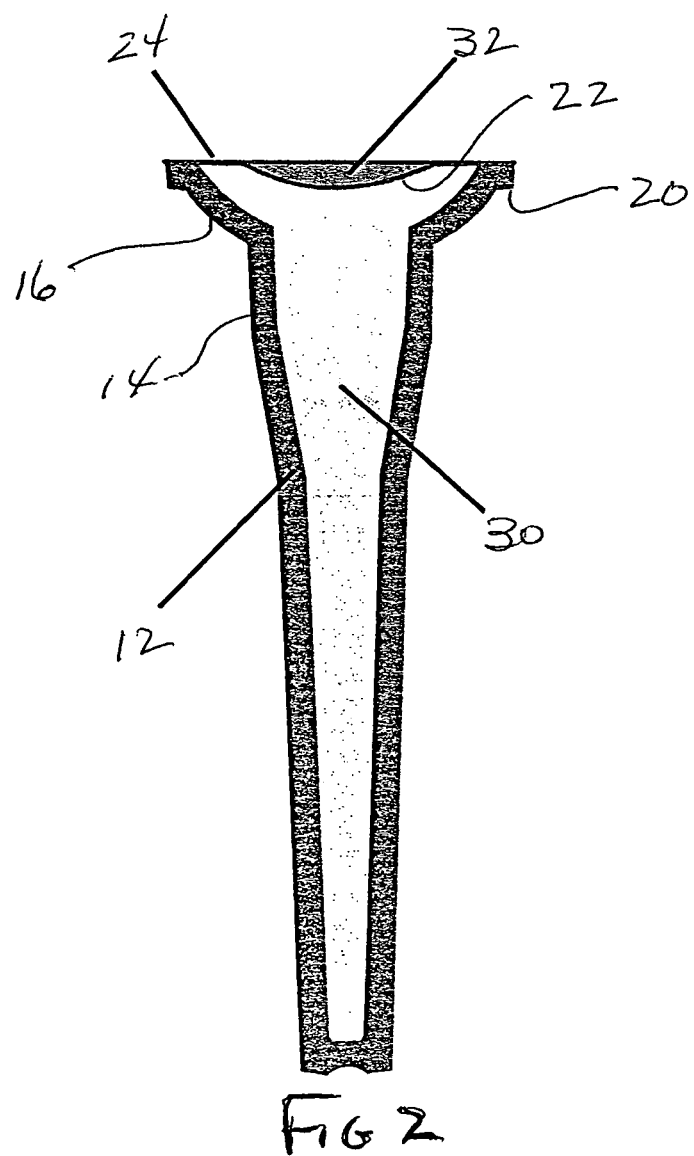
FIG. 2 is a cross sectional view of the needle guard of FIG. 1.

FIGS. 2 and 3 depict a first embodiment of the needle guard 10, which has a hollow needle sheath 12, the hollow interior being closed at a first, lower end of the needle guard 10 and opened at a second, upper end. The needle sheath 12 is generally tapered from a greater diameter at the upper end to a lesser diameter at the lower end. This tapered design facilitates receiving the needle 110 of the syringe and needle assembly 100 while using a minimal amount of adhesive, but it would be evident to one of ordinary skill in the art that a straight design would work with equal effectiveness. From the upper end of needle sheath 12, the needle guard 10 is expanded in diameter, typically tapering outwardly from the upper end of needle sheath 12 to form a hollow luer lock/hub sheath 14. From the upper end of the luer lock/hub sheath 14, the needle guard 10 further expands to a funnel or bowl shaped receptor 16 which tends to guide the needle 110, luer lock 112 and hub 108 into the interior of the needle guard 10. Relief grooves 18 are formed in the interior walls of the luer lock/hub sheath 14 to allow passage of adhesive, as will be detailed hereinbelow. A lip 20 may surround the perimeter of receptor 16, as will be detailed hereinbelow.

The hollow interior of the needle sheath 12 and luer lock/hub sheath 14 is filled with a first, base element 30 of a two part, fast curing adhesive. One type of adhesive which could be used in the present invention is cyanoacrylate. The needle guard 10 is sealed at its open end by an inner membrane 22 and a outer membrane 24. Between the inner membrane 22 and outer membrane 24 is a pocket filled with a second, activator adhesive element 32, such as amine, with the first membrane 22 keeping the base element 30 and the activator element 32 separate until such time as the needle guard is used. Both the inner membrane 22 and outer membrane 24 are typically of a metal foil, although other suitable membranes, such as a plastic, rubber or a laminate, which does not react with either the base adhesive element 30 or activator adhesive element 32 could be used with equal effectiveness without departing from the spirit of the present invention.

Preferably, the needle guard 10 is formed of a polypropylene, but it would be evident to one of ordinary skill in the art that other materials could be used with equal effectiveness without departing from the spirit of the present invention.

It would be evident to one of ordinary skill in the art, that while cyanoacrylate and amine are cited, other base adhesive an activator elements could be used with equal effectiveness, without departing from the spirit of the present invention.

Figure 4:
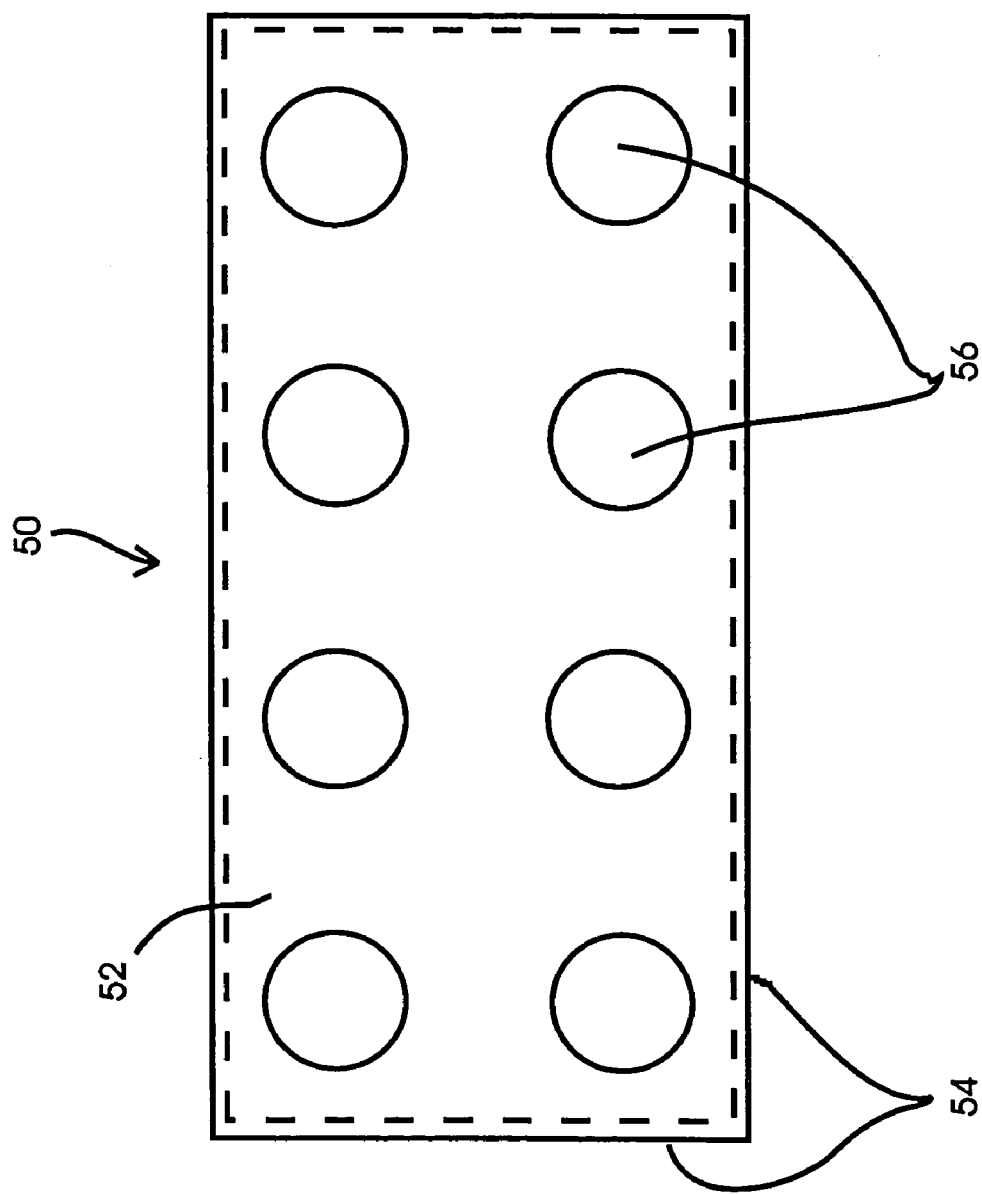
FIG. 4 is a plan view of the needle guard stand of the present invention.
Figure 5:
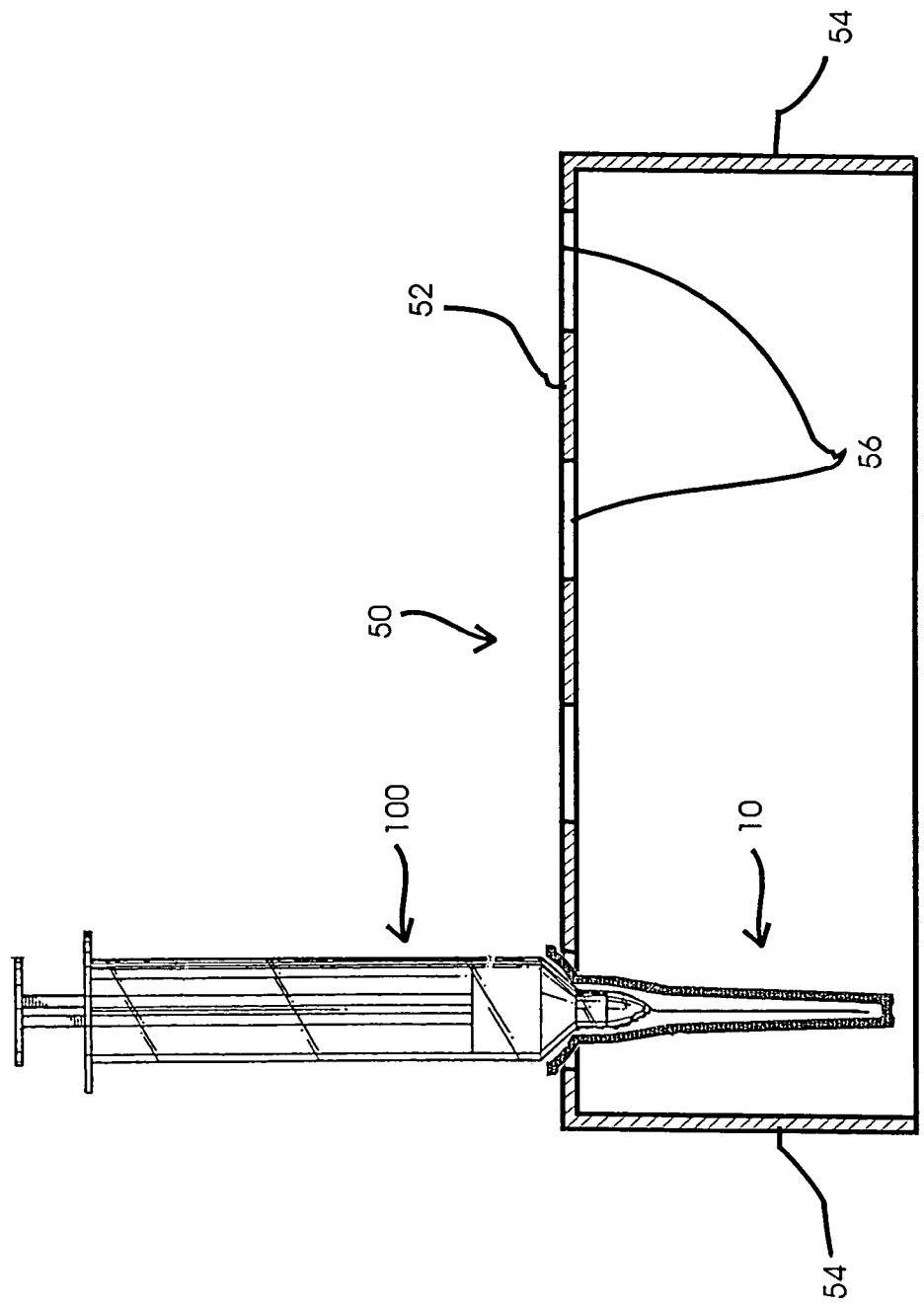
FIG. 5 is a cross sectional view of the stand of FIG. 4 with the needle guard and syringe and needle assembly of FIG. 1 inserted therein.

A needle guard stand 50 having a top surface 52 and at least three riser elements 54 is depicted at FIGS. 4 and 5. The top surface 52 may generally be of any shape, although a substantially rectangular surface 52 is depicted. The surface 52 has at least one, and generally a plurality of apertures 56 formed therethrough, each aperture 56 being capable of holding one needle guard 10. The riser elements 54 are of sufficient height for the needle guards 10 to be suspended by their lips 20, through the apertures 56, from the surface 52. It would be evident to one of ordinary skill in the art that the at least three riser elements 54 could be individual legs or a continuous peripheral wall extending downwardly from surface 52. For use with a second embodiment of the needle guard 10b described hereinbelow, the apertures 56 would be substantially rectangular.

It would be evident to one of ordinary skill in the art that a single central riser element 54 could be utilized in the above cited embodiment, but stability of the needle guard stand 50 would be compromised by so doing.

In use, a needle guard 10 is dropped into one of a plurality of the apertures 56 formed in the surface 52 of the needle guard stand 50. The needle guard 10 should be intact, filled with the base adhesive element 12 and activator adhesive element 32 separated by the inner membrane 22 and sealed by the outer membrane 24. After using the syringe and needle assembly 100, the syringe body 102 is held in one hand while the needle 110 is inserted into the needle guard 10, the needle puncturing the outer membrane 24, passing through the activator adhesive element 32 and then puncturing the inner membrane 22. As the inner membrane 22 is punctured, the needle 110 continues through the interior of the luer lock/hub sleeve 14 and into the needle sleeve 12, while the activator adhesive element 32 coats the surfaces of the needle 110, luer lock 112 and syringe end 108 es they pass through the activator adhesive element 32. Contact of the activator adhesive element 32 with the base adhesive element 30 causes almost instantaneous curing of the adhesive 30/32. Relief grooves 18 formed in the interior walls of the luer lock/hub sleeve 14 allows the base adhesive element 30 to escape to the receptor 16 area as the luer lock 112 enters the leur lock/hub sleeve 14, allowing the mixture of the base adhesive element 30 and activator adhesive element 32. With the syringe and needle assembly 100 fully inserted into the needle guard 10, the luer lock 112 and hub 108 are encased in cured adhesive 30/32 within the needle sleeve and the end of the syringe body 102 within the receptor 16.

The above-cited needle guard 10 and needle guard stand 50, along with the procedure for use meet all of the OSHA requirements for safe disposal of used syringes and needles.

Figure 6:
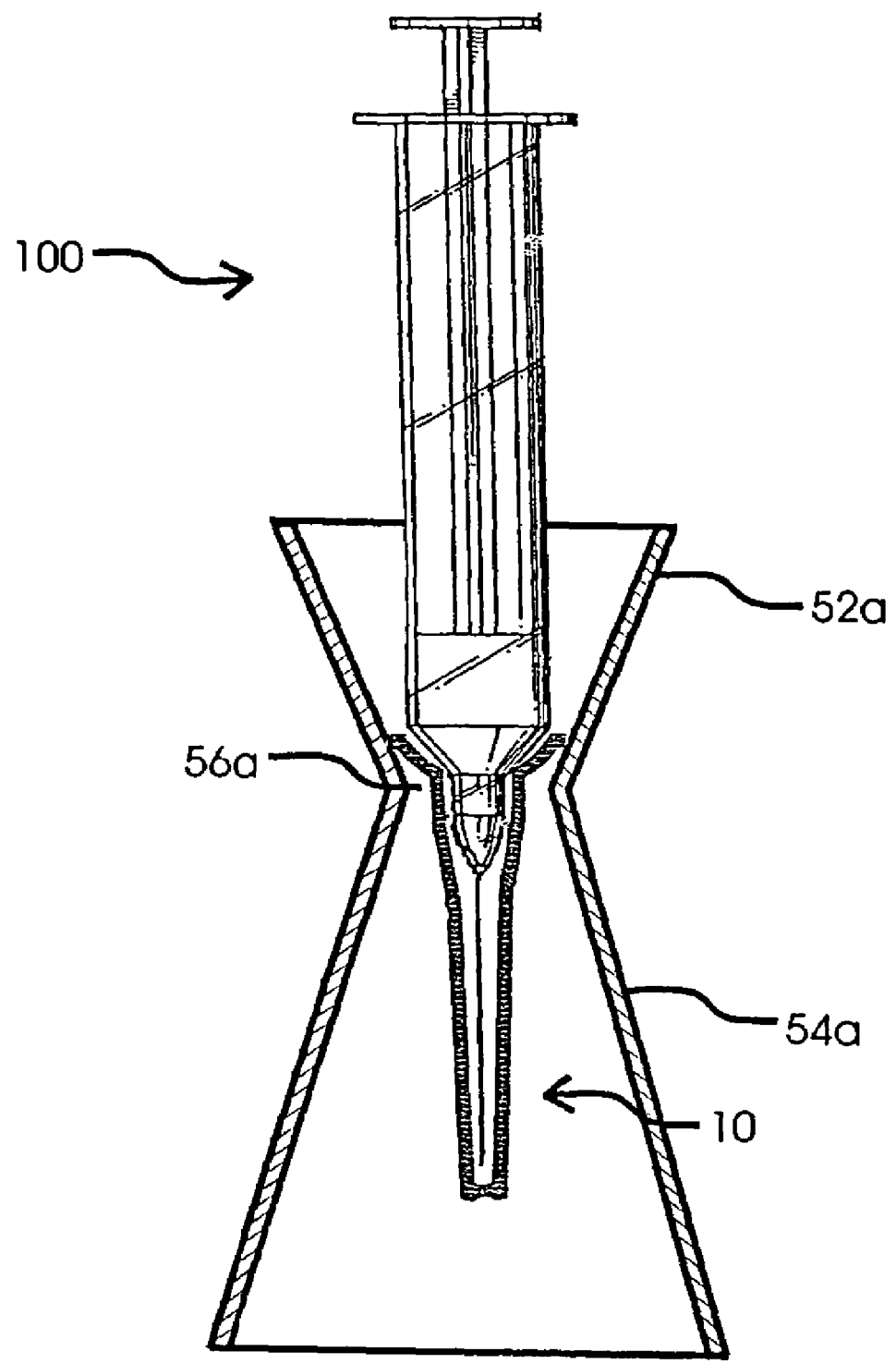
FIG. 6 is a cut away side elevational view of a second embodiment of the needle guard stand with the needle guard and syringe and needle assembly of FIG. 1 inserted therein.
Figure 8:
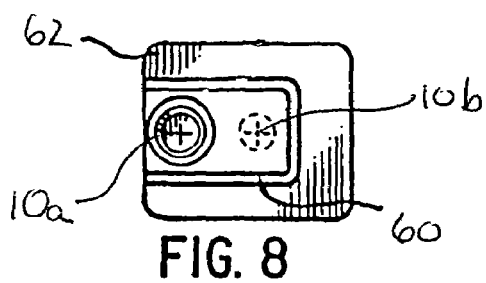
FIG. 8 is a plan view of the needle guard block of FIG. 7.
Figure 7:
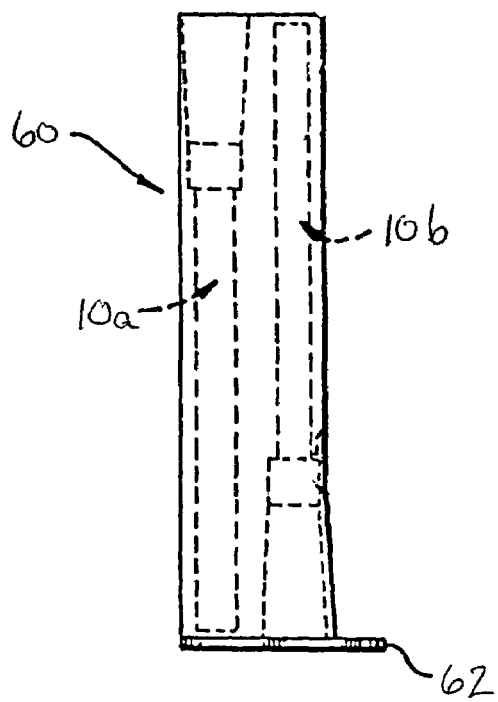
FIG. 7 is a side elevational view of the needle guard block of a second embodiment of the present invention.
Figure 9:
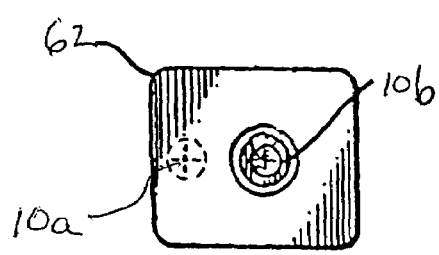
FIG. 9 is a bottom view of the needle guard block of FIG. 7.

A second embodiment of an individual needle guard stand 50a is disclosed at FIG. 6. Intended primarily for home use, the individual needle guard stand 50a is essentially a double cone, with the two cones joined at their vertexes. A riser cone 54a raises an aperture 56a formed at the juncture of the riser cone 54a and an upper cone 52a to a height sufficient that a needle guard 10 can be suspended from the juncture into the interior of the riser cone 54a. The upper cone 52a, which would typically have a height less than that of the riser cone 54a, aids in directing the needle 110 of a syringe and needle assembly 100 into the top of the needle guard 10. This configuration gives a steady base and aiming guide for safe, one-handed disposal for those who might have trouble using the needle guard 10 and needle guard stand 50. It would be evident to one of ordinary skill in the art that, while a double cone is disclosed, the lower portion of the needle guard stand 50a could be configured in a variety of shapes without departing from the spirit of the present invention.

A second embodiment of the needle guard of the present invention is depicted at FIGS. 7 thru 10, as needle guard block 60. As the functional elements of the needle guards 10 and 10b are substantially identical, the description of interior elements and method of use will not be repeated, but rather, only the exterior housing of the second embodiment will be described.

The needle guard 10b is formed within a substantially rectilinear needle guard block 60, which houses both a shipping needle guard 10a, internally similar to standard needle guards covering new needles, and a disposal needle guard 10b, shipping needle guard 10a and disposal needle guard 10b being formed from the opposite ends of the needle guard block 60. A lip 62 surrounds a first end of the needle guard block 60 the first end being that from which the disposal needle guard 10b is formed. When a syringe and needle assembly 100 is assembled, the needle guard block 60 is placed over the needle 110 such that the needle 110, luer lock 112 and syringe hub 108 are all firmly housed within the shipping needle guard 10a. When the syringe and needle assembly 100 are to be used, the syringe and needle assembly 100 is withdrawn from the shipping needle guard 10a and the needle guard block 60 is dropped into a needle guard stand 50, being suspended from the top surface 52 of the needle guard stand 50 by lip 62. After the syringe and needle assembly 100 has been used, it may be inserted into the disposal needle guard 10b, as described hereinabove.

It is to be understood that the present invention is not limited to the embodiments described above, but encompasses any and all embodiments within the scope of the following claims.

What is claimed is:

1. A non-mechanical needle guard kit for permanently securing and incapacitating a single used syringe and needle assembly comprising:

at least one needle guard, each needle guard comprising:
a sleeve for receiving a hypodermic needle and luer lock and the hub and end of a syringe barrel attached thereto, and two part adhesive securing means for securing said needle and luer lock and said hub and syringe end within said sleeve,
whereby said securing means incapacitates said syringe and needle assembly and adhesively bonds said syringe barrel and needle assembly to said needle guard when said syringe and needle assembly are fully inserted into said sleeve; and
stand means for removably holding at least one of said needle guards in a stable, upright position, thereby allowing one handed securing and incapacitation of said syringe and needle assembly within said needle guard.

2. A non-mechanical needle guard kit for permanently securing and incapacitating a single used syringe and needle assembly, as defined in claim 1, wherein each at least one needle guard further comprises a receptor chamber adjoining an open, upper end of said disposal sleeve, and said two adhesive securing means comprises:

a first, base adhesive element of a two part adhesive disposed in said disposal sleeve of said needle guard,
an inner and an outer membrane sealingly and punctureably sealing said needle guard, said inner and outer membranes having a pocket formed therebetween, said pocket having a second, activator adhesive element disposed therein and said inner membrane separating said base adhesive element from said activator adhesive element,
whereby, when said needle and luer lock and said hub and syringe end enter said needle guard, said outer membrane and said inner membrane are punctured, thereby allowing said base adhesive element and said activator adhesive element to mix and set, permanently securing said syringe and needle assembly within said needle guard.

3. A non-mechanical needle guard kit for permanently securing and incapacitating a single used syringe and needle assembly, as defined in claim 2, wherein said disposal sleeve further comprises at least one relief groove formed in the interior wall thereof, said at least one relief groove allowing said base adhesive element to pass around said luer lock, hub and syringe end as they pass into said disposal sleeve, thereby ensuring a solid bond between said luer lock, hub and syringe end with said disposal sleeve.

4. A non-mechanical needle guard kit for permanently securing and incapacitating a single used syringe and needle assembly, as defined in claim 3, wherein an open, upper end of said receptor terminates in a lip, and said stand means comprises:

a substantially horizontal surface supported by at least three riser elements, said horizontal surface further comprising at least one aperture formed therein, each of said at least one aperture dimensioned to receive one of said needle guards, suspending said needle guard by said lip of said needle guard.

5. A non-mechanical needle guard kit for permanently securing and incapacitating a single used syringe and needle assembly, as defined in claim 3, wherein said needle guard further comprises:

a second sleeve for removably receiving the hypodermic needle and luer lock and the hub and end of a new, unused syringe for storage before use attached thereto, such that when said second sleeve is removed from said new syringe, said needle guard may be placed in said stand means such that said first sleeve is in position to receive said needle and luer lock and said hub and syringe end for disposal.

6. A non-mechanical needle guard kit for permanently securing and incapacitating a single used syringe and needle assembly, as defined in claim 3, wherein said stand means comprises an upper element having a substantially conical internal surface which tapers down to a single aperture at its center, said upper element being supported by at least one riser element and said conical internal surface aiding in directing a needle into said needle guard.

7. A non-mechanical needle guard kit for permanently securing and incapacitating a single used syringe and needle assembly, as defined in claim 2, wherein said inner membrane is positioned across the uppermost edge of said of said open, upper end of said disposal sleeve, and said outer membrane is positioned above and substantially adjacent said inner membrane with said pocket formed by a gap formed between at least a central portion of said inner membrane and said outer membrane.

8. A non-mechanical needle guard kit for permanently securing and incapacitating a single used syringe and needle assembly, as defined in claim 6, wherein the at least one riser element of the stand means comprises a base, said base having a lower end with a diameter that is substantially larger than the diameter of the single aperture of the upper element, thereby providing a stable support for said stand means and said needle guard, which stability will be maintained despite forces to which it can be expected to be subject during the course of inserting a needle and syringe within said needle guard positioned within said stand means.

* * * * *